United States Patent [19]

Panzani

[11] Patent Number: 5,358,482
[45] Date of Patent: Oct. 25, 1994

[54] SINGLE-NEEDLE EXTRACORPOREAL PLASMAPHERESIS CIRCUIT

[75] Inventor: Ivo Panzani, Mirandola, Italy

[73] Assignee: Roerig Farmaceutici Italiana S.R.L., Mirandola, Italy

[21] Appl. No.: 133,769

[22] Filed: Oct. 7, 1993

Related U.S. Application Data

[63] Continuation of Ser. No. 793,767, Nov. 18, 1991, abandoned.

[30] Foreign Application Priority Data

Nov. 22, 1990 [IT] Italy .................... 22146 A/90

[51] Int. Cl.$^5$ ............................................. A61M 37/00
[52] U.S. Cl. .................................................... 604/6; 604/4
[58] Field of Search ................. 604/4, 5, 6, 7, 19, 604/27; 210/321.6, 321.65, 321.66, 321.71

[56] References Cited

U.S. PATENT DOCUMENTS

| | | | |
|---|---|---|---|
| 3,902,490 | 9/1975 | Jacobsen et al. | 604/5 X |
| 3,908,653 | 9/1975 | Kettering | 604/5 |
| 4,086,924 | 5/1978 | Latham, Jr. | 604/6 |
| 4,231,366 | 11/1980 | Schael | 604/4 |
| 4,464,144 | 8/1984 | Troutner et al. | 604/5 |
| 4,568,327 | 2/1986 | Seufert | 604/5 |
| 4,605,503 | 8/1986 | Bilstad et al. | 210/651 |
| 4,648,866 | 3/1987 | Malbrancq et al. | 604/5 |
| 4,655,742 | 4/1987 | Vantard | 604/6 |
| 4,687,580 | 8/1987 | Malbrancq et al. | 210/651 |
| 4,842,576 | 6/1989 | Lysaght et al. | 604/6 |
| 4,954,128 | 9/1990 | Ford | 604/5 |

Primary Examiner—Sam Rimell
Attorney, Agent, or Firm—Thomas E. Popovich; David B. Edgeworth

[57] ABSTRACT

Single-needle extracorporeal plasmapheresis circuit, has a filter in which plasma is separated from the blood with a membrane subject to transmembrane pressure. Two connections to the filter in the blood circuit include one connection of a line to a single needle. An interposed pump is in that line. The other connection has another line to a blood reservoir. A further line connects the plasma side of the filter membrane to a plasma collection bag. Another pump in the further line is controlled by an automatic control means suitable for maintaining the transmembrane pressure in the filter at a value within an optimum range for the entire duration of the plasmapheresis process.

10 Claims, 1 Drawing Sheet

SINGLE-NEEDLE EXTRACORPOREAL PLASMAPHERESIS CIRCUIT This is a continuation of application Ser. No. 07/793,767 filed Nov. 18, 1991, now abandoned.

FIELD OF THE INVENTION

The invention relates to a single-needle extracorporeal plasmapheresis circuit.

BACKGROUND OF THE DISCLOSURE

It is known that plasmapheresis consists in removing blood from a donor or from a patient to introduce it in an extracorporeal circuit which comprises a filter in which a liquid fraction, called plasma, is separated from the blood mass which contains the cell fraction which is then reintroduced into the donor or patient; the plasma is then kept, in the case of removal from a donor, or eliminated if it is taken from a patient in order to replace it.

In proceeding with a single-needle extracorporeal circuit, the process includes a series of cycles, each of which has a blood withdrawal step and a subsequent step for the reintroduction of the fraction which remains after plasma separation, which ends when the plasma collection reaches the required amount.

In the extracorporeal circuits more commonly comprised within the known devices and methods, the filter in which the plasma is separated from the blood has a blood circuit connected at one end to a line provided with a pump connected to a single needle and at the other end to a line which leads into a blood collection reservoir, and is furthermore provided with a plasma container connected by a line to a plasma collection bag.

The extracorporeal circuit thus configured allows a plasmapheresis process in which the plasma is separated from the blood exclusively during the steps of removal of the blood from the patient or donor, whereas during the subsequent reinfusion steps no plasma separation is performed and the plasma container is simply clamped to prevent pumping plasma or other liquids which are present in the system.

Such processes therefore have the disadvantage of one active step out of two for each of the cycles, only one active step out of two, and of consequently entailing long cycle times, which are particularly unpleasant if the plasmapheresis relates to a donor.

The known devices also include a type of extracorporeal circuit in which there is a line for recirculating part of the blood through a filter during reinfusion, but with this method there is the risk of not operating within the optimum range of pressures of the fluids present in the system, resulting in a decrease in the efficiency of the system. The larger amount of blood not reinfused to the patient or donor leads to a decrease in the amount of fresh blood which can be drawn during a subsequent step.

The aim of the present invention is thus to provide a single-needle extracorporeal plasmapheresis circuit which, by operating with the maximum possible efficiency, allows a drastic reduction in the time required for carrying out the plasmapheresis process.

SUMMARY OF THE DISCLOSURE

This aim is achieved by a single-needle extracorporeal plasmapheresis circuit according to the invention, which comprises a filter in which plasma is separated from the blood due to the presence of a preset transmembrane pressure between the blood and plasma. Two connections are on the blood circuit; one connection being connected to a line which ends at the single needle and has an interposed pump, the other connection being a line to a blood reservoir. A line fit between the plasma in of the filter and a plasma collection bag has a pump controlled by an automatic control means suitable for maintaining the preset transmembrane pressure across a membrane in the filter at an optimum range of values for the entire duration of the process of plasmapheresis.

Further characteristics and advantages will become apparent from the description of a preferred but not exclusive embodiment of the invention, illustrated only by way of non-limitative example in the accompanying drawings, wherein:

DETAILED DESCRIPTION OF THE DRAWINGS

Figure 1:
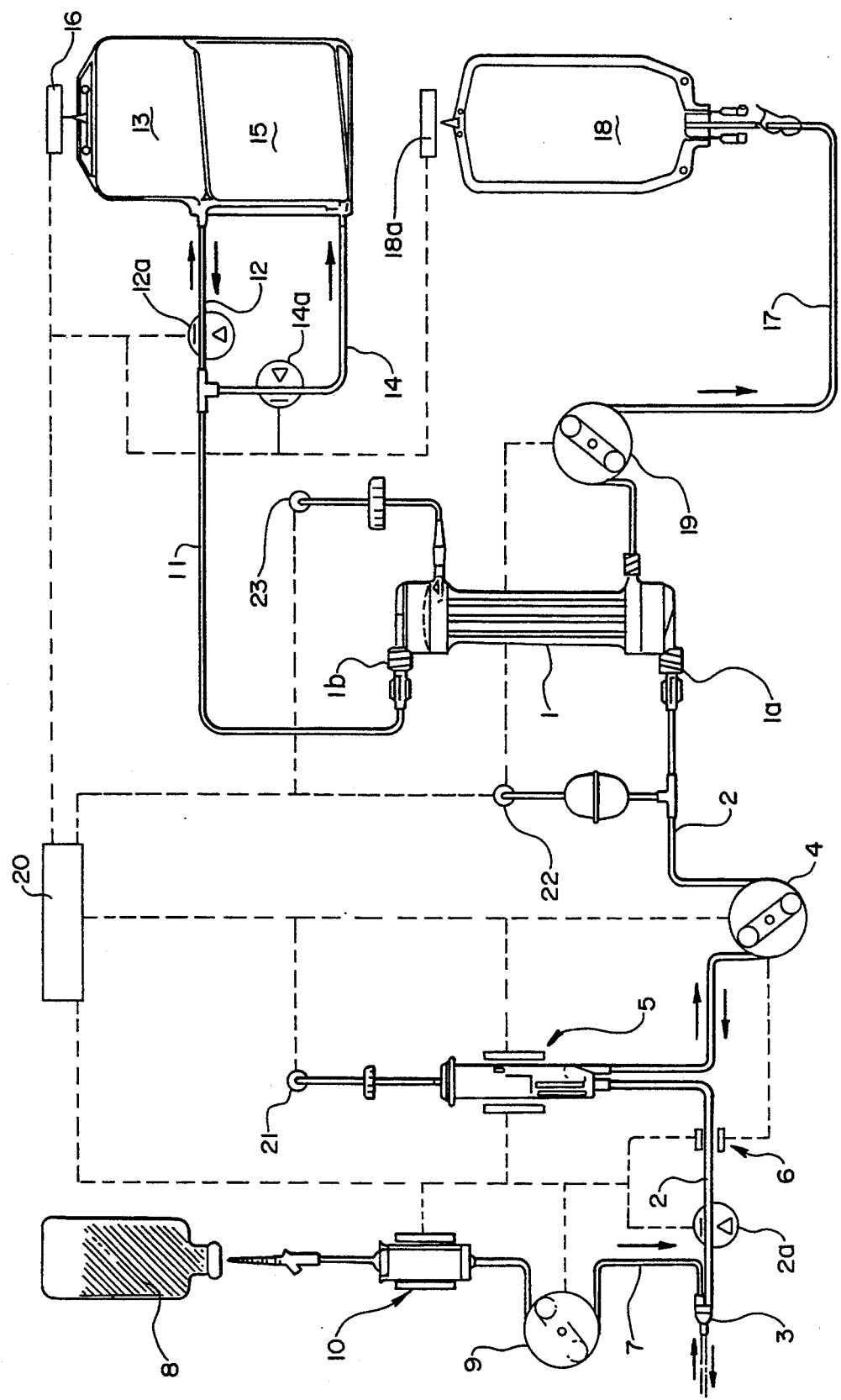
FIG. 1 is a schematic view of an extracorporeal circuit.

With reference to FIG. 1, the reference numeral 1 indicates a filter having a membrane through which plasma is separated from the blood taken from a donor or from a patient. The presence of a transmembrane pressure, between blood and plasma is the difference between the average pressure in the blood circuit and the average pressure in the plasma contained inside the filter. The transmembrane pressure must be maintained at a preset level.

The filter 1 has two connections in the blood circuit; the first connection designated by 1a, is connected to the line 2 which ends at single needle 3. Line 2, can be shut off or closed by means of an electric solenoid clamp 2a. A blood pump 4 is interposed between connection 1a and single needle 3.

A level sensor 5 and a bubble sensor 6 are each connected in series with line 2. Another line 7 is connected to the single needle 3 and conveys anticoagulant solution drawn from a bottle 8 by means of a pump 9. A bottle depletion control 10 is interposed between bottle 8 and pump 9 as a safety precaution.

A second connection in the blood circuit of the filter 1, designated by 1b, connects line 11 which branches into two lines. Line 12, which can be shut off or closed by means of an electric solenoid clamp 12a, attaches to a blood collection reservoir 13, which is made in the shape of a bag. That bag ensures a pressure value equal to that of the atmospheric pressure therein, thus eliminating a need for detecting the internal bag pressure. Consequently, the system is simplified.

Line 14, which can be shut off or closed by means of an electric solenoid clamp 14a attaches to the priming source 15.

An automatic system 16 for weighing the reservoir 13 and source 15 is shown schematically in FIG. 1.

An important feature is provided by line 17, which connects to the plasma side of filter 1 to a plasma collection bag 18. Line 17 has a plasma pump 19, which is controlled by automatic control means connected to a microprocessor 20 thereby maintaining in the filter 1 the transmembrane pressure at the preset level, i.e. a substantially constant value within an optimum operating range for filter 1 during the entire duration of a plasmapheresis process. Therefore, the transmembrane pressure remains the same during the removal steps and during the reinfusion steps. An automatic system for weighing 18a is shown for bag 18 in FIG. 1.

The signals detected by the sensors 5 and 6, by the bottle depletion control 10 and by the weighing systems 16 and 18a, together with those of the system pressure transducers 21, 22 and 23, reach a microprocessor 20, which is programmed to analyze information from the sensors and control the pumps 9, 4 and 19 and the electric clamps 2a, 12a and 14a thereby automatically operating the entire system. In FIG. 1, the broken lines represent the various electrical connections between the sensors and the microprocessor 20 of the control system.

The operation of the invention is as follows:

After the initial priming step and with washing liquid in the bag 15, a plasmapheresis process may begin with a removal step during which the blood, drawn by the pump 4, is supplied to the filter 1, by line 2. A certain amount of plasma is separated while the transmembrane pressure is maintained substantially constant. Operation of pump 19 ensures the constant transmembrane pressure by removing plasma and sending it to the collection bag 18. Residual blood leaves the filter 1, enters the lines 11 and 12 and collects in the bag 13.

The substantially constant value of the transmembrane pressure is maintained within the optimum operating range of the system in the filter 1 by the action of the pump 19. The transmembrane pressure does not drop below the minimum values for the good efficiency of filter 1 and does not exceed the maximum values above which blood hemolysis risks arise.

The removal step ends when a preset amount of blood in the bag 13 is reached, and the step of reinfusion of the blood contained in the bag 13 to the patient or donor begins with the reversal of the direction of rotation of the pump 4, to send the blood along the reversed path through the filter 1.

The pump 19 operates during this reinfusion step as well, so as to maintain the transmembrane pressure in the filter 1 at an optimum value which is preset by the operator, and therefore plasma separation continues during this reinfusion step as well and the pump 19 conveys plasma to the bag 18.

When the bag 13 is completely empty, the reinfusion step ends and a new cycle starts in a manner identical to the one described; the removal and reinfusion steps thus follow one another and are adjusted by the circuit control of the system according to microprocessor 20 until the required amount of plasma has been collected in the bag 18; at this point the process stops.

The described operating condition is quite favorable, since the dual separations of plasma from blood during the removal steps and during the reinfusion steps allows an increase in the efficiency of the filter and consequently a drastic reduction in the time required for the process with respect to what occurs in the known devices and methods.

The following numerical example is provided to show the importance of the invention.

Assume one wishes to remove from a donor or patient an amount equal to 600 ml (milliliters) of plasma, removing 300 ml of blood during each of two cycles.

Assuming a 20% efficiency of the filter, by working according to the most common known devices and procedures with plasma separation only during the removal step, a plasma volume equal to 300 ml×0.20=60 ml is obtained for each cycle.

Therefore, 600 ml÷60 ml=10 cycles which are necessary in order to collect the required 600 ml of plasma.

Things proceed quite differently with the extracorporeal circuit according to the invention, as is apparent by examining the amount of plasma collected for each cycle for an equal volume of removed blood, i.e. 300 ml, and for an equal efficiency of the filter, i.e. 20%.

During the removal step, the plasma collection is again 300 ml×0.20=60 ml, as with the known devices and methods, but plasma is now processed and obtained also during the step of reinfusion of the 300 ml−60 ml=240 ml of blood which remains. An amount of plasma equal to 240 ml×0.20=48 ml is separated during reinfusion.

During each cycle, therefore, one obtains 60 ml+48 ml=108 ml of plasma, and therefore, the required 600 ml of plasma are collected with a process which comprises only 600 ml÷108 ml=approximately 6 cycles, as opposed to the 10 cycles required when one operates with the previously described process.

As mentioned, the achieved time saving almost halves which is truly considerable.

The described invention is susceptible to numerous modifications and variations, all of which are within the scope of the inventive concept: thus, for example, the control system can allow, during operation, a certain variability in the transmembrane pressure in the filter 1, while maintaining the value within the optimum operating range.

In the practical execution of the invention, the materials employed, as well as the shapes and dimensions, may be any according to the requirements of a skilled practitioner; all the details may furthermore be replaced with other technically equivalent elements.

What is claimed is:

1. An extracorporeal plasmapheresis circuit for separation of plasma from blood, comprising:
    (a) a needle for connecting to a blood source;
    (b) plasma separation means for separating plasma from blood, the plasma separation means divided by a membrane into a blood side and a plasma side;
    (c) a first line connecting the needle to the blood side of the plasma separation means;
    (d) a blood reservoir connected by a second line to the blood side of the plasma separation means;
    (e) a plasma reservoir connected by a third line to the plasma side of the plasma separation means;
    (f) a first pump connected to the first line between the needle and the plasma separation means for pumping blood from the needle to the blood side of the plasma separation means;
    (g) a second pump connected to the third line between the plasma reservoir and plasma side of the plasma separation means for pumping plasma from the plasma side of the plasma separation means to the plasma reservoir wherein a transmembrane pressure from the blood side to the plasma side of the membrane is established; and
    (h) control means operably connected to the first and second pumps for maintaining the transmembrane pressure at a preset level.

2. The extracorporeal plasmapheresis circuit of claim 1 further including a first pressure transducer connected to the first line between the needle and the blood side of the plasma separation means and a second pressure transducer connected to the plasma side of the plasma separation means, wherein the first and second pressure transducers are operably connected to the control means.

3. The extracorporeal plasmapheresis circuit of claim 1 wherein the first pump is reversible for pumping blood from the blood reservoir, through the plasma separation means, and to the needle.

4. The extracorporeal plasmapheresis circuit of claim 1 further including a priming source and a fourth line connecting the priming source to the second line.

5. The extracorporeal plasmapheresis circuit of claim 2 further including a first clamp connected to the first line between the needle and the plasma separation means and a second clamp connected to the fourth line between the priming source and the second line, wherein the first and second clamps are operably connected to the control means.

6. The extracorporeal plasmapheresis circuit of claim 1 further including an anticoagulant reservoir, a fifth line connecting the anticoagulant reservoir to the first line, and a third pump connected to the fifth line between the anticoagulant reservoir and the first line for pumping anticoagulant into the blood being pumped from the needle to the blood side of the plasma separation means.

7. The extracorporeal plasmapheresis circuit of claim 1 further including a bubble sensor operably connected to the first line.

8. The extracorporeal plasmapheresis circuit of claim 2 further including a first weighing system connected to the blood reservoir for determining when a predetermined amount of blood is collected in the blood reservoir, wherein the first weighing system is operably connected to said control means.

9. The extracorporeal plasmapheresis circuit of claim 2 including a second weighing system connected to the plasma reservoir for determining when a predetermined amount of plasma is collected in the plasma reservoir, wherein the second weighing system is operably connected to the control means.

10. A method for separating plasma from blood in an extracorporeal plasmapheresis circuit, comprising the steps of:
(a) drawing blood from a blood source through a needle;
(b) transporting the blood through a first line to a membrane filter;
(c) separating plasma from the blood in the membrane filter;
(d) transporting the filtered blood through a second line to a blood reservoir;
(e) transporting the separated plasma through a third line to a plasma reservoir;
(f) maintaining the transmembrane pressure across the membrane filter at a pre-set level by controlling a first pump connected to the first line and a second pump connected to the third line; and
(g) returning the filtered blood from the blood reservoir through the membrane filter, to the blood source.

* * * * *